(12) United States Patent
Häcker et al.

(10) Patent No.: US 12,144,913 B2
(45) Date of Patent: Nov. 19, 2024

(54) DIALYSIS MACHINE HAVING SECURITY AGAINST CONFUSION FOR HYDRAULIC CONNECTORS

(71) Applicant: Fresenius Medical Care Deutschland GmbH, Bad Homburg (DE)

(72) Inventors: Jürgen Häcker, Neu Neu-Ansprach (DE); Peter Scheunert, Friedrichsdorf (DE); Oliver Bond, Sennfeld (DE); Winfried Brehm, Hofheim (DE); Martin Kaiser, Haßfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1052 days.

(21) Appl. No.: 16/767,177

(22) PCT Filed: Nov. 28, 2018

(86) PCT No.: PCT/EP2018/082887
§ 371 (c)(1),
(2) Date: May 27, 2020

(87) PCT Pub. No.: WO2019/106039
PCT Pub. Date: Jun. 6, 2019

(65) Prior Publication Data
US 2020/0384175 A1    Dec. 10, 2020

(30) Foreign Application Priority Data
Nov. 28, 2017 (DE) ..................... 10 2017 128 080.4

(51) Int. Cl.
*A61M 1/16* (2006.01)
*A61M 39/10* (2006.01)

(52) U.S. Cl.
CPC ........ *A61M 1/1601* (2014.02); *A61M 1/1654* (2013.01); *A61M 39/10* (2013.01); *A61M 2039/1005* (2013.01); *A61M 2205/18* (2013.01)

(58) Field of Classification Search
None
See application file for complete search history.

(56) References Cited

U.S. PATENT DOCUMENTS

| 5,589,070 A | 12/1996 | Maltais et al. |
| 2003/0168120 A1* | 9/2003 | Brehm ................ A61M 1/1668 141/313 |

(Continued)

FOREIGN PATENT DOCUMENTS

| DE | 4303372 | 8/1994 |
| DE | 102013112038 | 4/2015 |

(Continued)

*Primary Examiner* — Jonathan M Peo
(74) *Attorney, Agent, or Firm* — Jacobson Bolman PLLC

(57) ABSTRACT

A dialysis machine has two hydraulic connectors at the dialysate side to which a respective connection line having a filter coupling is connected for connection to a dialyzer, with the hydraulic connectors being an inflow connector for feeding fresh dialysis liquid to the dialyzer and a backflow connector for draining consumed dialysate from the dialyzer. The dialyzer machine also has two parking positions associated with the respective hydraulic connectors for storing the filter couplings when not in operation, wherein the filter couplings of both hydraulic connectors are equipped with a connection sensor which recognizes a connecting of the filter coupling to a dialyzer and/or that both parking positions are provided with separate covers.

8 Claims, 3 Drawing Sheets

(56) References Cited

U.S. PATENT DOCUMENTS

2016/0051742 A1\* 2/2016 Strohhöfer ............ A61M 1/367
　　　　　　　　　　　　　　　　　　　　　　210/85
2016/0243298 A1\* 8/2016 Weisen ............... A61M 1/1692

FOREIGN PATENT DOCUMENTS

DE　　　102015122347　　　6/2017
EP　　　　　2131891　　　12/2009

\* cited by examiner

DIALYSIS MACHINE HAVING SECURITY AGAINST CONFUSION FOR HYDRAULIC CONNECTORS

The invention relates to a dialysis machine having an inflow connector for feeding fresh dialysis liquid to the dialyzer, having a backflow connector for draining consumed dialyzate from the dialyzer, and having two parking positions respectively associated with one connector, wherein a security against confusion is provided that ensures a storing of the inflow connector and of the backflow connector at the respective associated parking positions.

BACKGROUND

The dialyzer interface is a fluidic interface of a dialysis machine on which increased hygienic demands are made. The dialyzer has two hydraulic connectors at the dialyzate side. One serves as the inflow for fresh dialysis fluid, the other for leading off the consumed dialyzate. Consumed dialyzate is potentially infectious. When dismantling after a treatment, dialyzate moves onto the parking positions or parking connectors of the machine. Currently which connector is to be plugged to which parking position is indicated via a color code (for example, red to red and blue to blue). If a mix up arises here due to incorrect handling, there is a risk that the inflow coupling will be contaminated. On a subsequent treatment, pathogenic organisms could then move onto the hydraulic side of the dialyzer.

It is the object of the invention to provide a dialysis machine with which such a confusion can be reliably precluded.

BRIEF DESCRIPTION OF THE INVENTION

Against this background, the invention relates to a dialysis machine having two hydraulic connectors at the dialyzate side to which a respective connection line having a filter coupling is connected for connection to a dialyzer, with the hydraulic connectors being an inflow connector for feeding fresh dialysis liquid to the dialyzer and a backflow connector for draining consumed dialyzate from the dialyzer, and having two parking positions associated with the respective hydraulic connectors for storing the filter couplings when not in operation. Provision is made that the filter couplings of both hydraulic connectors are equipped with a connection sensor which recognizes a connecting of the filter coupling to a dialyzer and/or that both parking positions are provided with separate covers.

Suitable covers include cover flaps or sliding covers, for example. The parking position typically comprises a short-circuit connector to which the filter coupling is connected to be able to flush the system when not in operation.

DETAILED DESCRIPTION OF THE INVENTION

Figure 1:
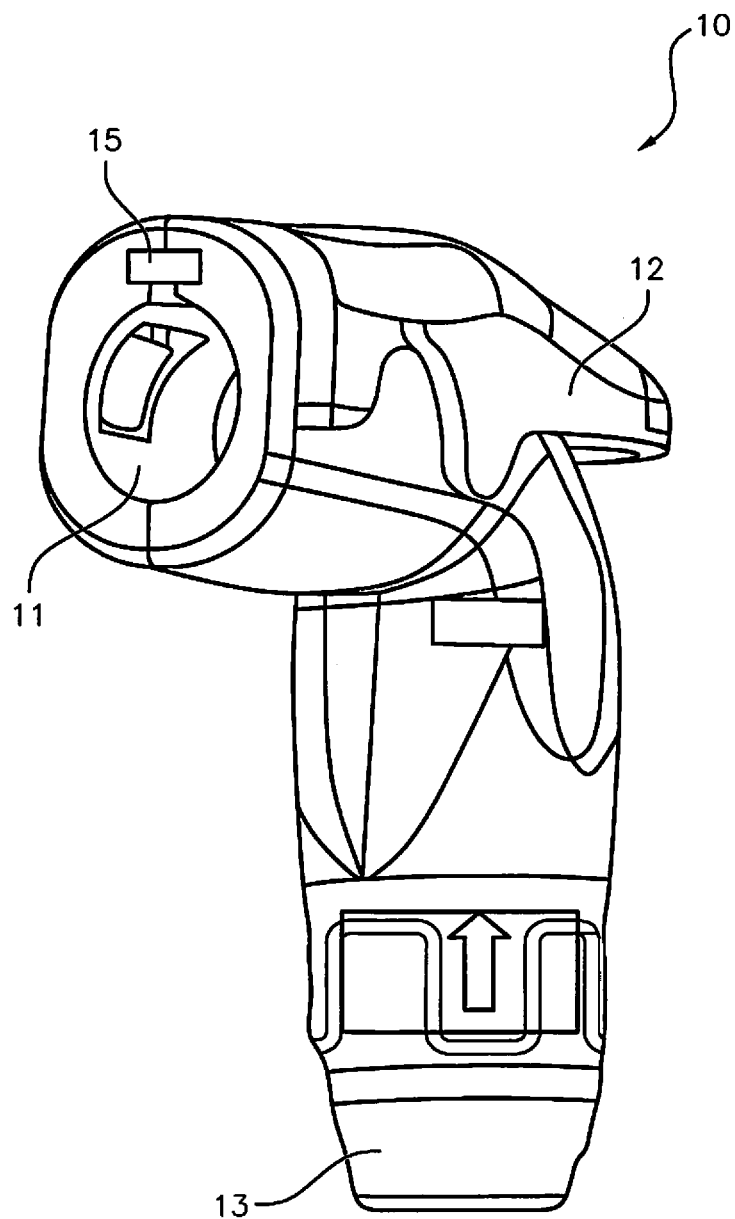
FIG. 1 shows a filter coupling of a dialysis machine in accordance with the invention.

Provision is made in an embodiment that the dialysis machine has releasable latch mechanisms for locking the covers of the parking positions. Examples of such a latch mechanism include electromagnetic or electromechanical latches.

Provision is made in an embodiment that the dialysis machine has cover sensors for recognizing the position of the covers of the parking positions.

Provision is made in an embodiment that the dialysis machine has actuators for opening and closing the covers of the parking positions. Examples of suitable actuators include electric motors.

Provision is made in an embodiment that the dialysis machine has s signal unit for outputting warning signals. Suitable warning signals include acoustic and visual warning signals.

Provision is made in an embodiment that the dialysis machine has a control unit that is connected to the connection sensors and preferably furthermore to the latching mechanisms, to cover sensors, and/or to actuators. The connection can be wireless or wired.

Provision is made in an embodiment that the control unit is configured such that when the disconnecting of a filter coupling from the dialyzer is recognized, the parking position associated with the respective hydraulic connector is or remains released and/or the parking positions not associated with the respective hydraulic connector is or remains blocked. It can be ensured in this manner in the dismantling process, that is when separating the dialyzer and the dialysis machine, that the filter couplings are stored at the correct parking positions.

If the dialysis machine has releasable latching mechanisms for blocking the covers of the parking positions, the control unit can be configured such that when a disconnecting of the filter coupling from the dialyzer is recognized, the latching mechanism of the parking position associated with the respective hydraulic connector is or remains released and/or the latching mechanism of the parking position not associated with the respective hydraulic connector is or remains blocked.

If the dialysis machine has actuators for opening and closing the covers of the parking positions, the control unit can be configured such that when a disconnecting of the filter coupling from the dialyzer is recognized, the cover of the parking position associated with the respective hydraulic connector is opened or remains open and/or the cover of the parking position not associated with the respective hydraulic connector is or remains closed.

If the dialysis machine has cover sensors for recognizing the position of the covers of the parking positions and if it furthermore has a signal unit, the control unit can be configured such that a warning signal is output on recognition of a disconnecting of the filter coupling from the dialyzer when the cover of the parking position not associated with the respective hydraulic connector is open or opened.

Provision is made in an embodiment that the control unit is configured such that when an opening of the cover of a parking position is recognized, the latching mechanism of the cover of the other parking position is blocked until a connecting of that filter coupling to a dialyzer is recognized whose associated parking position was released by opening the cover. It can be ensured in this manner in the assembling process, that is on the connection of the dialyzer and of the dialysis machine, that a filter coupling is not accidentally led back to the wrong parking position during handling.

Against the initially named background, the invention furthermore relates to a method of separating a dialyzer from a dialysis machine in accordance with the invention, wherein when the disconnecting of a filter coupling from the dialyzer is recognized, the parking position associated with the respective hydraulic connector is or remains released and/or the parking position not associated with the respective hydraulic connector is or remains blocked.

The invention furthermore further relates to a method of connecting a dialyzer to a dialysis machine in accordance with the invention, wherein when an opening of the cover of a parking position is recognized, the latching mechanism of the cover of the other parking position is blocked until a connecting of that filter coupling to a dialyzer is recognized whose associated parking position was released by opening the cover.

Figure 2:
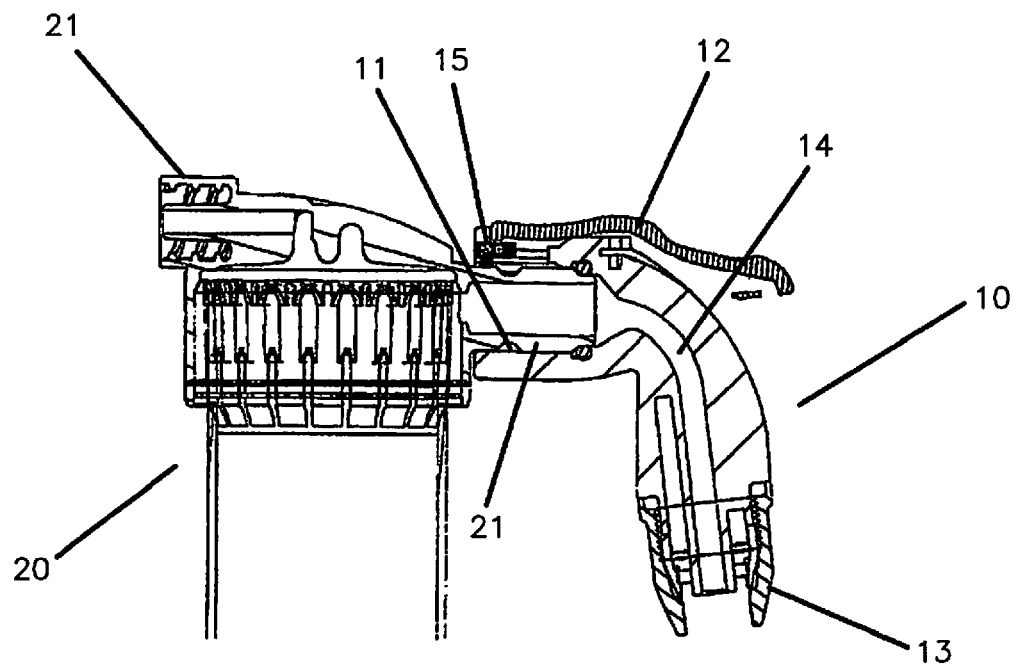
FIG. 2 shows the filter coupling of FIG. 1 in a state connected to the dialyzer.

Further details and advantages of the invention result from the following embodiment described with reference to the Figures. There are shown in the Figures:

FIG. 1: a filter coupling of a dialysis machine in accordance with the invention;

FIG. 2: the filter coupling of FIG. 1 in a state connected to the dialyzer; and

Figure 3:
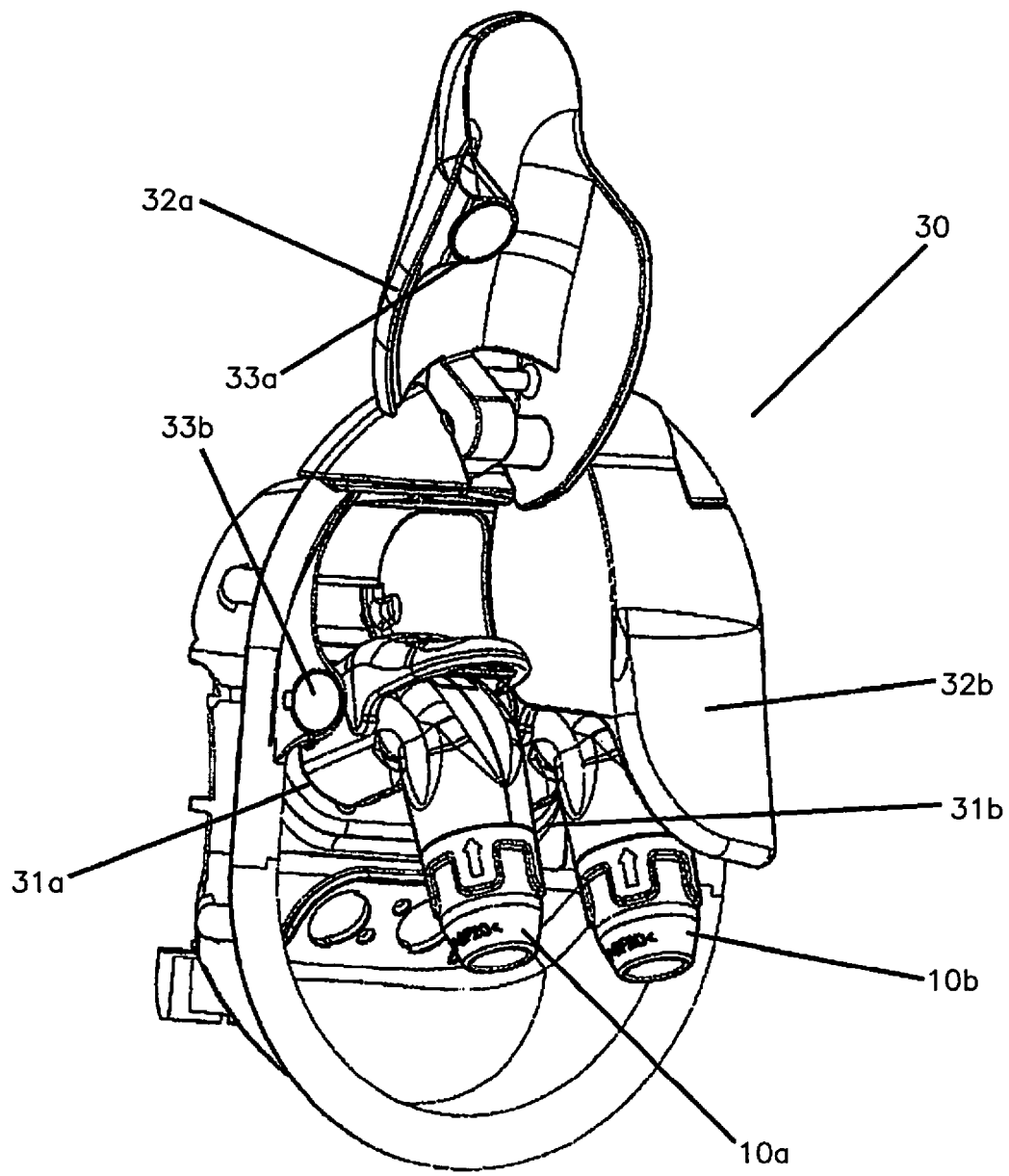
FIG. 3 shows a parking station of a dialysis machine in accordance with the invention.

FIG. 3: a parking station of a dialysis machine in accordance with the invention.

BRIEF DESCRIPTION OF THE DRAWINGS

The filter couplings 10 of the example of a dialysis machine in accordance with the invention shown in the Figures are configured to be manually connected to connectors 21 of a dialyzer 20. The dialysis machine comprises two such filter couplings, one for connecting to the inflow connector of the dialyzer and one for connecting to the backflow connector of the dialyzer.

The filter couplings 10 comprise a female socket 11 into which a male connector 21 of a dialyzer 20 can be plugged. An actuating lever 12 serves to release and fix the mount 11 to the connector 21. A connection region 13 for a liquid hose is located at the opposite side of the filter couplings 10. A fluid passage 14 is formed between the mount 11 and the connection region 13. The connection sensor 15 that is seated in the mount 11 and that can recognize a connection of the filter coupling 10 to the connector 21 is characteristic of the present invention. It is, for example, a contact sensor here. It can be connected to the control unit of the dialysis machine wirelessly or using a connection wire, not shown.

Short-circuit connectors 31a and 31b for both filter couplings 10a and 10b of the dialysis machine are located at a parking or short-circuit station 30 of the dialysis machine. Each of these short-circuit connectors 31a and 31b is covered by a separate cover flap 32a and 32b respectively. The cover sensors 33a and 33b serve the recognition of the position of the respective cover flap 32a and 32b respectively. The dialysis machine further comprises electromagnetic latches, not shown in any more detail, for blocking the cover flaps 32a and 32b and electrical actuators, not shown in any more detail, for opening and closing the cover flaps 32a and 32b. The cover sensors 33a and 33b and equally the latches and actuators are connected to the control unit of the machine. The control unit is connected to a signal device that can output warning signals.

The filter couplings 10a/b are thus each connected to a respective connection sensor 15 in a dialysis machine in accordance with the invention, said connection sensor recognizing the connection position, i.e. the connection to a connector of a dialyzer 20. The short-circuit station 30 is furthermore divided and each short-circuit connector 31a and 31b is provided with a separate cover flap 32a and 32b respectively including a cover sensor 33. The short-circuit connectors 31a and 31b on which the filter couplings 10a and 10b respectively are deposited in non-operation or during the cleaning program are therefore equipped with a respective separate mechanical cover flap 32a and 32b respectively that can be actuated with individual monitoring.

The dismantling process, that is the separating of the dialyzer 20 from the dialysis machine, can take place as follows: One of the filter couplings 10 is individually released from the associated connector 21 of the dialyzer by the user. The connection sensor 15 recognizes which of the two couplings 10 has been disconnected and releases the associated short-circuit connector 31a/b or blocks the non-associated short-circuit connector 31a/b. Release can mean that (a) a latching of the flap 32a/b is canceled; (b) the flap 32a/b is automatically opened by means of an actuator; or (c) no warning signal is output when the flap 32a/b is manually opened. Blocking can mean that (a) the flap 32a/b is latched; or (b) a warning signal is output when the flap 32a/b is manually opened.

The assembly process, that is the connection of the dialyzer and of the dialysis machine, can take place as follows: A flap 32 is opened by the user. The cover sensor 33 recognizes which flap 32 is open and blocks, in the above sense, the other flap.

The invention claimed is:

1. A dialysis machine having
two hydraulic connectors at a dialyzate side to which a respective connection line having a filter coupling is connected for connection to a dialyzer, with the hydraulic connectors being an inflow connector for feeding fresh dialysis liquid to the dialyzer and a backflow connector for draining consumed dialyzate from the dialyzer, and having two parking positions associated with the respective hydraulic connectors for storing the filter couplings when not in operation, and
a control unit configured such that when disconnecting one of the filter couplings from the dialyzer is recognized, (i) the parking position associated with the respective hydraulic connector is or remains released and (ii) the parking position associated with the other hydraulic connector is or remains blocked,
characterized in that
the filter couplings of both hydraulic connectors are equipped with connection sensors, respectively, which recognize independently a connecting of the filter couplings, respectively, to the dialyzer, both parking positions are provided with separate covers, and the dialysis machine has releasable latching mechanisms for blocking the covers of the parking positions.

2. A dialysis machine in accordance with claim 1, characterized in that the dialysis machine has cover sensors for recognizing the position of the covers of the parking positions.

3. A dialysis machine in accordance with claim 2, characterized in that the dialysis machine has actuators for opening and closing the covers of the parking positions.

4. A dialysis machine in accordance with claim 1, characterized in that the dialysis machine has a signal unit for outputting warning signals.

5. A dialysis machine in accordance with claim 3, characterized in that the control unit is connected to the connection sensors and is further connected to one or more of the latching mechanisms, cover sensors, and actuators.

6. A dialysis machine in accordance with claim 5, characterized in that the control unit is configured such that when an opening of the cover of one of the parking positions is recognized, the latching mechanism of the cover of the other parking position is blocked until a connecting of the filter coupling associated with the one parking position to the dialyzer is recognized, which was released by opening the cover.

7. A method of separating the dialyzer from a dialysis machine in accordance with claim 1,
   characterized in that
   when disconnecting one of the filter couplings from the dialyzer is recognized, (i) the parking position associated with the respective hydraulic connector is or remains released and (ii) the parking position associated with the other hydraulic connector is or remains blocked.

8. A method of connecting the dialyzer to a dialysis machine in accordance with claim 1,
   characterized in that
   when an opening of the cover of one of the parking positions is recognized, the latching mechanism of the cover of the other parking position is blocked until a connecting of the filter coupling associated with the one parking position to the dialyzer is recognized, which was released by opening the cover.

\* \* \* \* \*